US009797824B2

(12) United States Patent
Wu et al.

(10) Patent No.: US 9,797,824 B2
(45) Date of Patent: *Oct. 24, 2017

(54) METHOD FOR HEMATOLOGY ANALYSIS

(71) Applicant: Abbott Laboratories, Abbott Park, IL (US)

(72) Inventors: Jiong Wu, Los Gatos, CA (US); Giacomo Vacca, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 159 days.

This patent is subject to a terminal disclaimer.

(21) Appl. No.: 14/808,725

(22) Filed: Jul. 24, 2015

(65) Prior Publication Data

US 2016/0018313 A1   Jan. 21, 2016

Related U.S. Application Data

(63) Continuation of application No. 13/093,502, filed on Apr. 25, 2011, now Pat. No. 9,097,704.

(60) Provisional application No. 61/331,516, filed on May 5, 2010, provisional application No. 61/331,867, filed on May 6, 2010.

(51) Int. Cl.
| | | |
|---|---|---|
| *G01N 15/14* | (2006.01) | |
| *G01N 21/64* | (2006.01) | |
| *G01N 35/10* | (2006.01) | |
| *G01N 33/50* | (2006.01) | |
| *G01N 33/58* | (2006.01) | |
| *G01N 15/10* | (2006.01) | |
| *G01N 15/00* | (2006.01) | |

(52) U.S. Cl.
CPC ....... *G01N 15/1434* (2013.01); *G01N 15/147* (2013.01); *G01N 21/6428* (2013.01); *G01N 33/5047* (2013.01); *G01N 33/5094* (2013.01); *G01N 33/582* (2013.01); *G01N 35/1002* (2013.01); *G01N 2015/0065* (2013.01); *G01N 2015/0069* (2013.01); *G01N 2015/1006* (2013.01); *G01N 2015/149* (2013.01); *G01N 2015/1486* (2013.01); *G01N 2021/6439* (2013.01)

(58) Field of Classification Search
None
See application file for complete search history.

(56) References Cited

U.S. PATENT DOCUMENTS

| | | | |
|---|---|---|---|
| 5,017,497 A | 5/1991 | Gerard de Grooth et al. |
| 5,138,181 A | 8/1992 | Lefevre et al. |
| 5,350,695 A | 9/1994 | Colella et al. |
| 5,516,695 A | 5/1996 | Kim et al. |
| 5,559,037 A | 9/1996 | Kim et al. |
| 5,631,165 A | 5/1997 | Chupp et al. |
| 5,648,225 A | 7/1997 | Kim et al. |
| 5,812,419 A | 9/1998 | Chupp et al. |
| 5,939,326 A | 8/1999 | Chupp et al. |
| 6,060,322 A | 5/2000 | Horton et al. |
| 6,197,593 B1 | 3/2001 | Deka et al. |
| 6,228,652 B1 | 5/2001 | Rodriguez et al. |
| 6,524,858 B1 | 2/2003 | Zelmanovic et al. |
| 6,551,831 B2 | 4/2003 | Gupta et al. |
| 6,579,685 B1 | 6/2003 | Russell et al. |
| 6,618,143 B2 | 9/2003 | Roche et al. |
| 6,955,872 B2 | 10/2005 | Maples et al. |
| 2003/0143117 A1 | 7/2003 | Nagai et al. |

FOREIGN PATENT DOCUMENTS

| | | |
|---|---|---|
| WO | 2009061710 | 5/2009 |
| WO | 2010126838 | 11/2010 |

OTHER PUBLICATIONS

BD LSR, Brochure, BD BioSciences, Jun. 2003.*
Telford et al., DPSS Yellow-Green 561-nm Lasers for Improved Fluorochrome Detection by Flow Cytometry, Cytometry Part A 68A:36-44 (2005).*
deGrooth et al., Light-Scattering Polarization Measurements as a New Parameter in Flow Cytometry, Cytometry 8:539-544, 1987.*
CELL-DYN Ruby RTM. [online] 2007 [retrieved on Nov. 25, 2007]. Retrieved from the Internet: http://www.abbottdiagnostics.com/Products/Instruments.sub.--by.sub.--Plat-form/default.cfm?sys.sub.--id=158>.
CELL-DYN Sapphire. Abbott Diagnostics Products [online], Abbott Laboratories, 2008 [retrieved on Nov. 25, 2007]. Retrieved from the Internet: http://www.abbottdiagnostics.com/Products/instruments_by_Platform/default.cfm?system=CELLDYN&suffix=Saffir.
CELL-DYN® 3200. Abbott Diagnostics Products [online]. Abbott Laboratories, 2008 [retrtieved on Nov. 25, 2007]. Retrieved from the Internet: http://www.abbottdiagnostics.com/Products/instruments%5Fby%5Fplatform/defaultcfm?sys_id=17.
Dako.pdf, Flow Cytometry Educational Guide, 2nd Edition, www.dako.com, 2006.

(Continued)

*Primary Examiner* — Taeyoon Kim
*Assistant Examiner* — Srikanth Patury
(74) *Attorney, Agent, or Firm* — Edward J. Baba; Bozicevic, Field & Francis LLP

(57) ABSTRACT

A method whereby one or more fluorescent dyes are used to bind and stain nucleic acids in certain blood cells, such as, for example, white blood cells, nucleated red blood cells, and reticulocytes, and to induce fluorescent emissions upon excitation of photons from a given source of light, such as, for example, a laser, at an appropriate wavelength. More particularly, this invention provides a method whereby a fluorescent trigger is used in a data collection step for collecting events that emit strong fluorescence, in order to separate white blood cells and nucleated red blood cells from red blood cells and platelets without the need for using a lysing agent.

21 Claims, 9 Drawing Sheets

(56) References Cited

OTHER PUBLICATIONS

Flow Cytometry Principles [online], [retrieved on Sep. 1, 2011]. Retrieved from the Internet: http://biology.berkeley.edu/crl/flow_cytometry_basic.html.
Flowguide, Introduction to Flow Cytometry: A Learning Guide, Technical Manual BD Biosciences, Apr. 2000.
McCoy et al. (1991) "Sorting minor subpopulations of cells: use of fluorescence as the triggering signal" Cytometry 12 (3):268-274.
SYTO-Dyes.pdf, Molecular Probes Handbook, Table 8.3, Jan. 2009.

\* cited by examiner

METHOD FOR HEMATOLOGY ANALYSIS

RELATED APPLICATIONS

The present application claims priority from of co-pending U.S. Provisional Patent Application No. 61/331,516, filed May 5, 2010 and co-pending U.S. Provisional Patent Application No. 61/331,867, filed May 6, 2010.

BACKGROUND OF THE INVENTION

1. Field of the Invention

This invention relates to a method for hematology analysis, wherein fluorescent dyes are used to distinguish various components of a sample of blood.

2. Discussion of the Art

The CELL-DYN® Sapphire™ automated hematology analyzer, as well as the CELL-DYN® 4000 automated hematology analyzer, both of which are commercially available from Abbott Laboratories, Santa Clara, Calif., are equipped with an optical bench that can measure multi-angle light scatter and fluorescence, as described in U.S. Pat. Nos. 5,631,165 and 5,939,326, both of which are incorporated herein by reference. Furthermore, U.S. Pat. Nos. 5,516,695 and 5,648,225, both of which are incorporated herein by reference, describe a reagent suitable for lysing red blood cells and staining nuclear DNA of membrane lysed erythroblasts to discriminate white blood cells from erythroblasts. Membrane lysed erythroblasts are erythroblasts wherein the membrane thereof has undergone lysis. U.S. Pat. No. 5,559,037, incorporated herein by reference, describes the simultaneous detection of erythroblasts and white blood cell differential by means of a triple triggering circuitry (AND/OR), which is used to eliminate noise signals from cell debris, such as, for example, membranes of lysed red blood cells, which are located below the lymphocyte cluster along the Axial Light Loss (ALL) axis of a cytogram. However, the use of lysing agents to lyse red blood cells brings about certain difficulties and complications in the detection of red blood cells and white blood cells. The lysing agent may be insufficiently strong, thereby resulting in red blood cells being counted as white blood cells. Alternatively, the lysing agent may be excessively strong, thereby resulting in artificially low counts of white blood cells. Different samples require lysing agents of different strengths in order to obtain accurate counts of white blood cells; accordingly, all hematology analyzers currently in use sometimes yield incorrect counts of white blood cells.

In hematological assays aimed at determining parameters from human whole blood, there are two physiological factors that present obstacles to simple, rapid, and accurate determination of cell counts. One factor is that, in typical fresh peripheral human whole blood, there are about 1,000 red blood cells and about 50 platelets for each white blood cell. The other factor is that, while platelets are typically sufficiently smaller than any other cell type to allow discrimination based on size, and most white blood cells are sufficiently larger than either red blood cells or platelets to again allow discrimination based on size, two cell species in particular—red blood cells and lymphocytes, a subtype of white blood cells—typically overlap in size distribution (as well as in their scattering signatures) to a sufficient degree to make discrimination based on size prone to gross error. Therefore, when determining red blood cells mainly by size discrimination, the asymmetry in concentration works in one's favor, since the occasional white blood cell misclassified as a red blood cell will not, generally, affect the overall accuracy of the measured concentration of red blood cells to any appreciable degree; however, the converse is not true, and any unaccounted for interference from red blood cells in determining the concentration of lymphocytes (and, by extension, the overall concentration of white blood cells) would yield very inaccurate results.

Consequently, methods have been developed in the prior art to handle this large asymmetry and size overlap and still provide useful results in an acceptable time frame. One standard method employed in the prior art has been to separate the blood sample to be analyzed into at least two aliquots, one destined for red blood cell and platelet analysis, and one for white blood cell analysis. The aliquot destined for white blood cell analysis is mixed with a reagent solution containing a lysing reagent that preferentially attacks the membranes of the red blood cells. Partially on account of their loss of hemoglobin through the compromised membrane, and partially on account of their attendant reduction in size, the resulting lysed red blood cells become distinguishable from lymphocytes based on their respective scattering signatures. Another method employed in the prior art involves using nucleic acid dyes to provide a fluorescent distinction between the red blood cells and the white blood cells. White blood cells contain a nucleus containing DNA. When these white blood cells are labeled via a fluorescent label, they can be distinguished from mature red blood cells, whose nuclei have been expelled in the maturation process.

Both of these methods have drawbacks. First of all, the lysing reagent used to dissolve the red blood cells can attack the white blood cells as well, reducing their integrity and eventually dissolving them. This drawback is magnified with fragile white blood cells, which are abnormal on account of some type of pathological condition (such, as, for example, chronic lymphocytic leukemia). Another drawback is attributable to certain types of red blood cells, such as, for example, those found in neonates, and in patients with thalassemia, sickle-cell anemia, and liver disease, which red blood cells are naturally resistant to lysis, and which red blood cells therefore tend to persist as interferents in white blood cell assays involving lysis. In order to reduce the likelihood of either degradation of white blood cells or interference from unlysed red blood cells (either of which would jeopardize the accuracy of the overall white blood cell concentration measurement), a carefully selected combination of a lysing agent, concentration of the lysing agent, control of temperature, and time of incubation must be used. In some cases, the user is offered several test options with different lysing conditions, thereby allowing the user to tailor the assay to the subject patient sample. This tailoring, however, is a complex solution, which additionally either requires prior knowledge of the state of the patient, or must be used as a reflex test following a standard complete blood count (CBC).

Turning to the previously mentioned fluorescence-based approach for discriminating red blood cells from lymphocytes, a major obstacle is the measurement rate. When white blood cells are measured at the same time as red blood cells and platelets, the presence of red blood cells sets an upper limit to the concentration that can be sent through the analyzer without incurring in coincidences at an unacceptably high rate; the dilution ratio used to achieve such concentration, in turn, limits the rate at which white blood cell events are being counted; and in order to obtain the counting precision expected of the analyzer, this relatively low rate of white blood cell event acquisition, in turn, results in long acquisition times. For example, the concept of measuring all of the components of blood from a single sample in one pass was disclosed in U.S. Pat. No. 6,524,858. As noted in that disclosure, the method would be capable of a cycle time of 88 seconds, or about 41 CBC/hr. This throughput is far lower than that achievable by most automated hematology analyzers commercially available today, severely limiting the commercial usefulness of the one pass method.

The CELL-DYN® Sapphire™ hematology analyzer, as another example, presently offers a test selection (requiring yet another aliquot of sample in addition to those used in the red blood cell/platelet assay and in the white blood cell assay) employing a nucleic-acid dye capable of differentiating between red blood cells and lymphocytes. This test selection uses the dye primarily to differentiate between mature red blood cells and reticulocytes, a subset of immature red blood cells that retain dye-absorbing RNA in the cytoplasm. While it would technically be possible to count the white blood cells using this same assay, because they are sufficiently differentiated by fluorescence from either red blood cells or reticulocytes to obtain the desired accuracy, the relatively low concentration of white blood cells in the dilution used makes it an impractical option to achieve the required statistical precision. Such a scheme would require an acquisition time of approximately 75 seconds, limiting throughput to only 48 CBC/hr. Accordingly, although this approach is theoretically feasible, a much higher throughput would be required in order for this approach to become practical commercially.

Although modern five-part differential hematology analyzers are capable of reporting more hematology parameters, and consequently, providing more useful diagnostics information, almost all of them contain sophisticated fluidic systems, reagent systems, and hardware systems in order to facilitate a number of different assays on blood samples of patients. The complex design often results in higher overall costs of hematology analyzers, as well as greater possibility of poor reliability of the hematology analyzers.

Red blood cells and platelets, as well as their associated parameters, are measured by means of impedance or optical methods, following a dilution of the blood sample with diluent. Quantification of hemoglobin requires lysis of red blood cells by means of a mixture of hemoglobin lysing reagent and, in most cases, a diluent. White blood cell count and white blood cell differential analysis rely on a separate reagent or reagents for lysing red blood cells, minimizing red blood cell fragments, and stabilizing white blood cells for differential measurement. Additional reagents, which may contain one or more fluorescent dyes, are needed to allow hematology analyzers to conduct more complete analysis of blood cells, including reticulocytes and nucleated red blood cells.

Therefore, it would be desirable to develop a method for identifying, analyzing, and quantifying the cellular components of a sample of whole blood by means of multi-angle light scatter without the need for lysing red blood cells, complex fluidic systems, complex reagent systems, or complex hardware systems.

SUMMARY OF THE INVENTION

This invention provides a method whereby one or more fluorescent dyes are used to bind and stain nucleic acids in certain blood cells, such as, for example, white blood cells, nucleated red blood cells, and reticulocytes, and to induce fluorescent emissions upon excitation of photons from a given source of light, such as, for example, a laser, at an appropriate wavelength. More particularly, this invention provides a method whereby a fluorescent trigger is used in a data collection step for collecting events that emit strong fluorescence, in order to separate white blood cells and nucleated red blood cells from red blood cells and platelets without the need for using a lysing agent.

In one embodiment, the method employs a plurality of optical channels and at least one fluorescent channel for collecting data and analyzing the data in order to identify each cell population and reveal additional information relating to a sample of blood.

The method described herein can reduce the complexity of hematology analyzers, which analyzers would require no more than two reagents for carrying out all hematology assays, including assays for determining reticulocytes and nucleated red blood cells. In addition, the fluidics components and hardware components, and consequently, overall cost, can be greatly reduced. More importantly, the error frequency of the hematology analyzer can also be greatly reduced. The lysis-free approach described herein eliminates the adverse effects of a lysing agent for red blood cells on samples of blood, including samples of blood containing lyse-resistant red blood cells and fragile white blood cells. It should be noted, however, that the method described herein can also be used when red blood cells undergo complete lysis or partial lysis.

BRIEF DESCRIPTION OF THE DRAWINGS

FIG. 8 is in a dot plot format.

FIG. 9 is in a contour plot format. FIG. 9 is based on the same white blood cell data as was used in FIG. 8.

DETAILED DESCRIPTION

Figure 2:
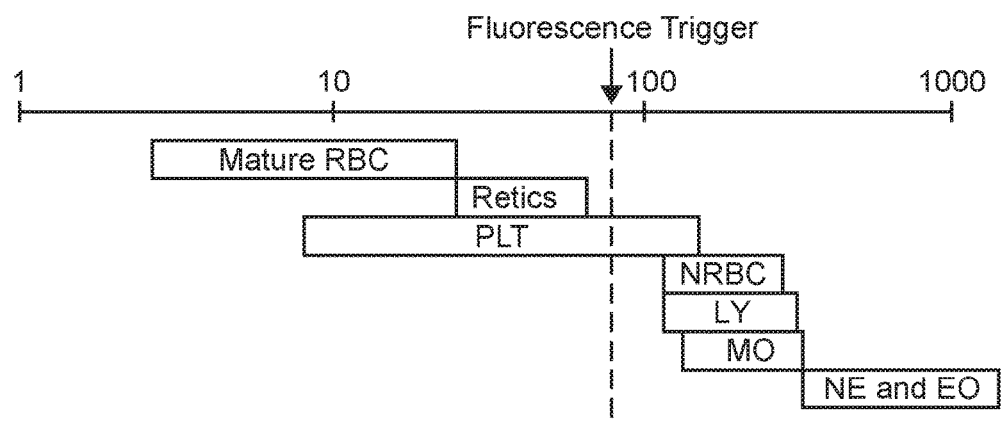
FIG. 2 illustrates a scheme for aiding in setting a fluorescent trigger. The horizontal scale represents a logarithmic scale ranging from a value of 1 to a value of 1000 for values of fluorescence. The values are arbitrary units.

As used herein the expression "axial light loss" and "ALL" refer to the measurement of the total light lost from the laser beam at from about 0° to about 1° when a particle passes through the beam. This parameter relates to measurement of light extinction, i.e., light lost through scattering as well as through absorption; in the absence of absorption, "axial light loss" is a measurement that correlates broadly with the sizes of cells or particles passing through an optical detection system. As used herein, the expressions "intermediate angle scatter" and "IAS" refer to the measurement of forward light scatter at intermediate angle from 3° to 10°. This parameter relates to measurement of complexity of a cell. As used herein, the term "complexity" refers to the composition of a cell. Some cells have mitochondria, ribosomes, nucleus, while other cells lack one or more of the foregoing components. The measured intensity of "IAS" depends to some degree on the heterogeneity of the contents of a cell (or particle) passing through the illumination beam of a cytometer. The density of "IAS" signals can be thought of as a measure of the complexity of the contents of the cell, i.e., the presence of organelles, such as, for example, nuclei, vacuoles, endoplasmic reticula, mitochondria, etc. As used herein, the expressions "polarized side scatter" and "PSS" refer to polarized light scatter at the angle of 90°. This parameter relates to measurement of lobularity. The nuclei of cells have various shapes that may result in one to five lobules, inclusive. A representative example of a cell with multi-lobed nucleus is a segmented neutrophil. As used herein, the expressions "depolarized side scatter" and "DSS" refer to depolarized light scatter at the angle of 90°. This parameter relates to measurement of subpopulations of blood cells. Blood cells have various numbers of subpopulations within the membranes of the cell. Examples of these subpopulations, for white blood cells, are eosinophils, neutrophils, basophils, monocytes and lymphocytes As used herein, the term "trigger" means the minimum value of a signal that a measurement of the signal must exceed to be considered valid. Events providing a signal value above the trigger value are collected and recorded. Events providing a signal value below the trigger value are ignored. With respect to the trigger values used herein, a scale of 0 to 5000 or a scale of 0 to 6000 is used for each channel of detection. Each value on the scale represents a gradation of the strength of a signal, with the value of 0 being the lowest strength and the value of 5000 (or 6000) being the highest strength. In FIG. 2, the scale is truncated at the value of 1000.

As used herein, the term "erythroblast" means any of the nucleated cells in bone marrow that develop into erythrocytes. As used herein, the term "erythrocyte" means the yellowish, non-nucleated, disk-shaped blood cell that contains hemoglobin and is responsible for the color of blood. As used herein, the expression "bright platelet" means a platelet that emits a relatively strong fluorescent signal. Bright platelets are collected in the white blood cell data block.

One or more detectors are preferably placed in the light path for measuring forward intermediate angle scattering (IAS) and either small angle forward scattering (SAS) or axial light loss (ALL). The light loss is generally due to scattering and defined as the decrease in light energy reaching a detector in the path of a laser beam due to the passage of a cell through that beam. Generally ALL is detected at an angle of from about 0° to about 1°. SAS is light energy that reaches a detector outside, but within a narrow angle of about 1° to about 3°, the incident laser beam due to scattering from a cell passing through the beam. A beam stop is generally provided to keep the laser beam from getting into the detector. ALL measuring systems collect light within the incident cone of laser illumination, while small angle scatter systems collect light outside this cone. In ALL measuring systems, the signal of interest is a negative signal subtracted from the steady state laser signal, whereas in the small angle forward scatter measurement, the signal is a small positive signal imposed on a very low background light level. Intermediate angle forward scattering (IAS) is similar to small angle forward scattering, except the light is scattered at a larger angle from the incident laser beam. More specifically, IAS relates to light scattered in a ring between 3° and 10° away from the incident or centerline of a laser beam. In a preferred embodiment, ALL is collected in the angles less than 0.3° horizontally and less than 1.2° vertically from the laser axis, and IAS is collected at angles between 3° and 10° from the laser axis.

As used herein, the expression "Open Mode" means that the sample is presented directly to the automated instrument by a human operator. As used herein, the expression "Closed Mode" means that the sample is presented directly to the automated instrument by a robotic mechanism.

As used herein, the expression "measuring cells" refers to enumerating cells by means of light scattering techniques to determine, for example, size, granularity, lobularity, and fluorescence when the cells are stained with a particular dye or fluorochrome.

The symbol "(s)" following the name of an object indicates that either the object alone or a plurality of the objects is being referred to, depending upon the context of the statement surrounding the mention of the object or objects.

As used herein, the expression "morphological assessment" means assessment of the shape of a cell. The term "leukocyte" means white blood cell. Unlike red blood cells, white blood cells occur in many different types. Examples of leukocytes include granulocytes, neutrophils, eosinophils, basophils, lymphocytes, and monocytes. The expression "reference method" means a method of the prior art against which a test method is compared. The term "sickle cell" means a red blood cell shaped like a sickle. A sickle cell is typically resistant to a lyse reagent. The term "thalassemic" relates to a genetic blood disorder in which the bone marrow cannot form sufficient red cells and red cell survival is also reduced. The term "lymphocyte" means a white blood cell that matures in lymph nodes, the spleen, and other lymphoid tissues, enters the blood, and circulates throughout the body. The expression "nucleated red blood cell" means an immature red blood cell that still contains a nucleus. As used herein, the term "noise" includes, but is not limited to, such substances as lysed red blood cells in particulate form, cell debris, and platelet clumps.

As used herein, the term "event" means a particle generating a signal that is sufficient to trigger at least one detector, such as, for example, the IAS detector, whereby that at least one detector signals the analyzer to collect measurements of that particle on all of the detectors enabled on the analyzer, e.g., ALL, IAS, PSS, and DSS. Particles include, but are not limited to, are white blood cells (WBC), red blood cells (RBC), red blood cell fragments, platelets (PLT), lipids, platelet (PLT) clumps.

As used herein, the terms and phrases "diluent", "sheath", and "diluent/sheath", and the like, mean a sheath diluent of the type suitable for use with CELL-DYN® Sapphire™, CELL-DYN® Ruby™, CELL-DYN® 3000 series, and CELL-DYN®4000 series hematology analyzers, which sheath diluents are commercially available from Abbott Laboratories, Santa Clara, Calif., and incorporated herein by reference.

As used herein, the term "data block" means data collected for a set of cells having similar populations, with respect to the number of cells per unit volume. For example, a given data block for a sample of blood can contain red blood cells (about $1 \times 10^6$ red blood cells/µL), reticulocytes (about $1 \times 10^4$ reticulocytes/µL), and platelets (about $1 \times 10^5$ platelets/µL). Another data block for a sample of blood can contain white blood cells (about $1 \times 10^3$ white blood cells/µL) and nucleated red blood cells (from about 10 to about 100 nucleated red blood cells/µL).

As used herein, the term "DNA" means deoxyribonucleic acid, which is a polymeric chromosomal constituent of living cell nuclei. As used herein, the term "RNA" means ribonucleic acid.

Automated hematology analyzers are discussed in WHITNEY WILLIAMS. Hem I Automated Cell Counting and Evaluation. Educational publication [online], [retrieved on 2008 Jul. 15]. Retrieved from the Internet: <URL: http://www.clt.astate.edu/wwilliams/new_page_4.html>, incorporated herein by reference. Representative examples of automated hematology analyzers suitable for use herein include, but are not limited to, CELL-DYN® Sapphire™ and CELL-DYN® Ruby™, modified by replacing the laser thereof with a laser having a wavelength ranging from about 350 nm to about 700 nm. CELL-DYN® hematology analyzers are commercially available form Abbott Laboratories, Santa Clara, Calif. It should be noted that any automated hematology analyzer based on the principle of flow cytometry can be modified to use a laser having a wavelength ranging from about 350 nm to about 700 nm.

The essential components of systems of the prior art include a source of light, a lens or system of lenses, a flow cell, and appropriate detectors. In both the prior art and in the method described herein, the sources of light, the lens and the systems of lenses, the flow cells, and the detectors, and the functions thereof in a flow cytometry system, are well-known to those of ordinary skill in the art. See, for example, U.S. Pat. Nos. 5,017,497; 5,138,181; 5,350,695; 5,812,419; 5,939,326; 6,579,685; 6,618,143; United States Patent Publication No. 2003/0143117 A1, and U.S. patent application Ser. No. 12/767,611, filed Apr. 26, 2010, and entitled METHOD FOR DISCRIMINATING RED BLOOD CELLS FROM WHITE BLOOD CELLS BY USING FORWARD SCATTERING FROM A LASER IN AN AUTOMATED HEMATOLOGY ANALYZER, where sources of light, lenses, flow cells, and detectors are described in greater detail. All of these references are incorporated herein by reference. See also http://biology.berkeley.edu/crl/flow_cytometry_basic.html, Mar. 30, 2006, pages 1-7, incorporated herein by reference. Lasers, lenses, flow cells, and detectors suitable for use in this invention are used in commercially available instruments from Abbott Laboratories, Santa Clara, Calif., under the trademark CELL-DYN®.

The method described herein involves an automated method for simultaneous analysis of white blood cell differential, erythroblasts, red blood cells, and platelets in liquid, such as, for example, blood. Other biological fluids, such as, for example, cerebrospinal fluid, ascites fluid, pleural fluid, peritoneal fluid, pericardial fluid, synovial fluid, dialysate fluid, and drainage fluid, can be used to determine various parameters of these fluids.

Figure 1:
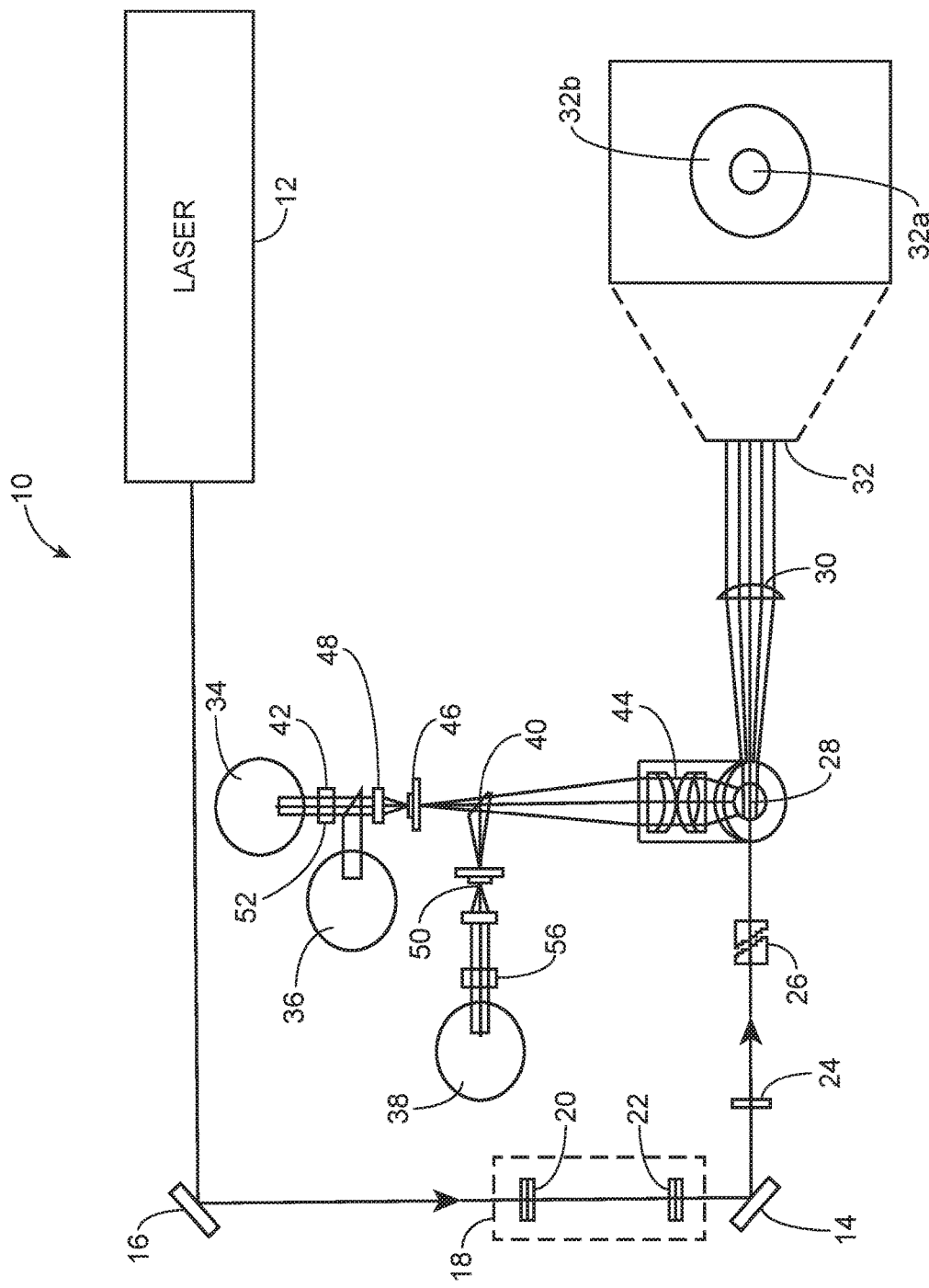
FIG. 1 is a schematic diagram illustrating the illumination and detection optics of an apparatus suitable for generating three-dimensional signals from cells for differential analysis.

Referring now to FIG. 1, an apparatus 10 comprises a source of light 12, a front mirror 14 and a rear mirror 16 for beam bending, a beam expander module 18 containing a first cylindrical lens 20 and a second cylindrical lens 22, a focusing lens 24, a fine beam adjuster 26, a flow cell 28, a forward scatter lens 30, a bulls-eye detector 32, a first photomultiplier tube 34, a second photomultiplier tube 36, and a third photomultiplier tube 38. The bulls-eye detector 32 has an inner detector 32a for 0° light scatter and an outer detector 32b for 7° light scatter.

In the discussion that follows, the source of light is preferably a laser. However, other sources of light can be used, such as, for example, lamps (e.g., mercury, xenon). The source of light 12 can be a vertically polarized air-cooled Coherent Cube laser, commercially available from Coherent, Inc., Santa Clara, Calif. Lasers having wavelengths ranging from 350 nm to 700 nm can be used. A laser actually constructed was a 407 nm laser purchased from Coherent. It should be noted that the laser was nominally designated to be a 405 nm laser, but the actual wavelength of the laser was 407 nm. A custom made mounting plate was designed for this laser in order to be compatible with the current optical bench of CELL-DYN® automated hematology analyzers. However, that particular mounting plate is not critical and other techniques for mounting can be used. Operating conditions for the 407 nm laser are substantially similar to those of lasers currently used with CELL-DYN® automated hematology analyzers.

Additional details relating to the flow cell, the lenses, the focusing lens, the fine-beam adjust mechanism and the laser focusing lens can be found in U.S. Pat. No. 5,631,165, incorporated herein by reference, particularly at column 41, line 32 through column 43, line 11. The preferred forward optical path system shown in FIG. 1 includes a spherical plano-convex lens 30 and a two-element photo-diode detector 32 located in the back focal plane of the lens. In this configuration, each point within the two-element photodiode detector 32 maps to a specific collection angle of light from cells moving through the flow cell 28. The detector 32 can be a bulls-eye detector capable of detecting axial light loss (ALL) and intermediate angle forward scatter (IAS). U.S. Pat. No. 5,631,165 describes various alternatives to this detector at column 43, lines 12-52.

The first photomultiplier tube 34 (PMT1) measures depolarized side scatter (DSS). The second photomultiplier tube 36 (PMT2) measures polarized side scatter (PSS), and the third photomultiplier tube 38 (PMT3) measures fluorescence emission from 440 nm to 680 nm, depending upon the fluorescent dye selected and the source of light employed. The photomultiplier tube collects fluorescent signals in a broad range of wavelengths in order to increase the strength of the signal. Side-scatter and fluorescent emissions are directed to these photomultiplier tubes by dichroic beam splitters 40 and 42, which transmit and reflect efficiently at the required wavelengths to enable efficient detection. U.S. Pat. No. 5,631,165 describes various additional details relating to the photomultiplier tubes at column 43, line 53 though column 44, line 4.

Sensitivity is enhanced at photomultiplier tubes 34, 36, and 38, when measuring fluorescence, by using an immersion collection system. The immersion collection system is one that optically couples the first lens 30 to the flow cell 28 by means of a refractive index matching layer, enabling collection of light over a wide angle. U.S. Pat. No. 5,631,165 describes various additional details of this optical system at column 44, lines 5-31.

The condenser 44 is an optical lens system with aberration correction sufficient for diffraction limited imaging used in high resolution microscopy. U.S. Pat. No. 5,631,165 describes various additional details of this optical system at column 44, lines 32-60.

The functions of other components shown in FIG. 1, i.e., a slit 46, a field lens 48, and a second slit 50, are described in U.S. Pat. No. 5,631,165, at column 44, line 63 through column 45, line 26. Optical filters 52 or 56 and a polarizer 52 or 56, which are inserted into the light paths of the photomultiplier tubes to change the wavelength or the polarization or both the wavelength and the polarization of the detected light, are also described in U.S. Pat. No. 5,631,165, at column 44, line 63 through column 45, line 26.

The photomultiplier tubes 34, 36, and 38 detect either side-scatter (light scattered in a cone whose axis is approximately perpendicular to the incident laser beam) or fluorescence (light emitted from the cells at a different wavelength from that of the incident laser beam).

Commercial hematology analyzers are intended for use on all whole blood specimens, including abnormal samples from patients. However, in reality, these analyzers may fail to provide accurate analyses for a small fraction of patient samples, especially for the samples having lyse-resistant red blood cells or fragile (lyse-sensitive) white blood cells. For samples having lyse-resistant red blood cells, unlysed red blood cells remain following the lysis procedure and thus result in a falsely high white blood cell count, and sometimes, a falsely high hemoglobin determination. For a sample having fragile white blood cells, the white blood cell differential may not be resolved properly, and some white blood cells (mostly lymphocytes) are destroyed or greatly adversely affected before the assay. Therefore, methods for adjusting the efficacy of lysing red blood cells have remained a great challenge in the field of hematology.

This invention provides a method for comprehensive analysis of blood, including complete blood count, white blood cell differential, counting reticulocytes, and counting nucleated red blood cells. No lysing agent is used to lyse red blood cells for white blood cell and hemoglobin measurements. The lysis-free approach simplifies the hematology analyzer. Such an approach requires the minimal number of reagents, and subsequently, much fewer components for hardware and fluidics. A single reagent could serve as both diluent and fluorescent dye, i.e., a diluent containing a pre-diluted fluorescent dye. Alternatively, two reagents can be used, namely, a diluent and a concentrated fluorescent dye. It should be noted, however, that the method described herein can also be used when red blood cells undergo complete lysis or partial lysis.

The method described herein uses of one or more fluorescent dyes to bind and stain nucleic acids in certain blood cells (e.g., white blood cells, nucleated red blood cells, and reticulocytes) and to induce fluorescent emissions upon excitation of photons from a given source of light, such as a laser, at an appropriate wavelength.

The method described herein uses at least one fluorescent trigger in the step of collecting data to collect events that emit strong fluorescence, in order to separate whole blood cells and nucleated red blood cells from red blood cells and platelets without the need for using a lysing agent.

The method described herein uses a plurality of optical channels and at least one fluorescent channel for collecting data and analyzing data in order to identify each cell population and reveal additional information, such as, for example, each population of cells, including reticulocytes, nucleated red blood cells, and major components of a white blood cell differential analysis.

All white blood cells and nucleated red blood cells have nuclei, which contain a relatively high density of DNA. Immature red blood cells, or reticulocytes, contain a network of ribosomal RNA. In contrast, mature red blood cells and platelets do not contain any nucleic acids. Therefore, a fluorescent dye can be selected to differentiate two classes of cells, those blood cells having nucleic acids and those blood cells not having nucleic acids. The fluorescent dye is intended to penetrate into live cells easily, bind DNA or RNA or both DNA and RNA with high affinity, and emit strong fluorescence with adequate Stokes shift if the dye is excited by an appropriate source of light. It is preferred that the fluorescent dye retain a significant percentage (preferably at least 10%, more preferably at least 50%) of the peak absorption of the fluorescent dye at the wavelength of the source of light in the visible band of the electromagnetic spectrum (approximately 400 nm to 700 nm) in order to be excited properly. A plurality of fluorescent dyes can also be used in the environment described herein. For example, the combination of a fluorescent dye capable of specifically binding to DNA and a fluorescent dye capable of specifically binding to RNA can be used to differentiate blood cells.

A fluorescent trigger is essential for collecting and analyzing white blood cells and nucleated red blood cells, both of which types of cells are present at relatively low concentrations, as compared with red blood cells and platelets. Mature red blood cells do not emit fluorescence or emit very weak autofluorescence. Reticulocytes emit stronger fluorescence than do mature red blood cells following RNA-dye interactions. Platelets in general should emit weak fluorescence, because most platelets do not contain nucleic acids. However, reticulated platelets (which contain RNA), and the possible attraction of dye molecules to surfaces of sticky platelets, may result in higher fluorescence emission on some platelets. Platelets may provide a broad range of fluorescent signals, ranging from as low as those of mature red blood cells to as high as those of lymphocytes. A small fraction of platelets can show strong fluorescent signals, with the result that these platelets are collected in the analysis of a white blood cell data block, because the values of the fluorescent signals from the platelets exceed the trigger value. See, for example, FIG. 2. The cells that show much stronger fluorescence emission are the cells having nuclei, i.e., all white blood cells and nucleated red blood cells. Accordingly, white blood cells and nucleated red blood cells can be separated from red blood cells and reticulocytes. A fluorescent trigger, usually set between reticulocytes and nucleated red blood cells or white blood cells, can be used to collect events involving white blood cells and nucleated red blood cells separately for further analysis. For example, reticulocytes have maximum fluorescent signal values of 50 in the detection system described herein. White blood cells have minimum fluorescent signal values of 150 in the detection system described herein. The trigger can be set at a fluorescent signal value between 50 and 150 in the detection system described herein. The optimal setting of the trigger would be 100 in the detection system described herein, but it is acceptable to set the fluorescent trigger value at, for example, 75 or 125 in the detection system described herein. The scheme of the fluorescent trigger is shown in FIG. 2. Two data blocks, one data block for all cells (predominantly red blood cells and platelets) and the other data block for white blood cells and nucleated red blood cells, can be generated with such a setting for a fluorescent trigger. When a fluorescent trigger is properly set, the hematology analyzer will only collect events emitting strong fluorescence, i.e., those signals from white blood cells and nucleated red blood cells, and a small fraction of bright platelets. Mature red blood cells and reticulocytes do not emit fluorescent signals of sufficient strength to be collected by the hematology analyzer. Thus, the fluorescent signals emitted by mature red blood cells and reticulocytes are not included in the second data block.

In another embodiment, all of the platelets can be stained by means of an appropriate fluorescent dye or by means of an appropriate staining procedure or by means of both an appropriate fluorescent dye and an appropriate staining procedure. By these means, platelets can be completely separated from all red blood cells, including reticulocytes, and captured as an independent population by using the fluorescent signals of the platelets, as well as by light extinction and scattering information.

In order to ensure that the fluorescence-based lysis-free method for performing hematology analysis functions properly, the fluorescent dye must substantially meet the following requirements:

(1) The fluorescent dye must be capable of being excited at the appropriate wavelength. It is not necessary that the peak absorption of the dye match exactly the wavelength of the source of light. It is preferred that the dye retain a significant fraction (at least about 10%, preferably at least about 50%) of its peak absorption at the appropriate wavelength. For example, the fluorescent dye SYTO® 41 has an absorption peak at approximately 412 nm. This dye retains strong absorption at 405 nm, i.e., $A_{405}/A_{412}$ is equal to approximately 90%.

(2) The fluorescent dye must provide strong fluorescence emission upon specifically binding to DNA or to RNA or to both DNA and RNA. The fluorescent dye itself, when not bound, emits very weak fluorescence. A fluorescent dye bound to a nucleic acid preferably emits at least 100×, more preferably emits at least 1000×, more fluorescence upon being excited by a source of light. A one-dye system (for staining both DNA and RNA) or a two-dye system (one dye for staining DNA staining, the other dye for staining RNA) can be employed.

(3) The fluorescent dye must provide an adequate Stokes shift. The fluorescence peak should differ from the absorption peak by at least 20 nm for collecting valid signals by the fluorescence detector (e.g., a photomultiplier tube).

(4) The fluorescent dye must exhibit good cell permeability. The dye molecules are required to easily penetrate cell membranes in order for the lysis-free assay to be effective.

(5) The fluorescent dye must have a high affinity for nucleic acids and must specifically bind to nucleic acids rapidly. Reaction kinetics should support the interaction between the dye and the nucleic acid when the dye penetrates the membrane of the cell.

(6) The fluorescent dye is preferably soluble in an aqueous solution. The dye should not precipitate upon further dilution thereof in aqueous solutions.

(7) The fluorescent dye must be stable in an aqueous solution or in an organic solution. Stability is required for manufacturing a dye reagent having an acceptable on-shelf life. Preferably, the dye reagent remains stable, i.e., substantially unchanged, for at least 12 months at ambient temperature.

The dyes suitable for use in the method described herein substantially meet the aforementioned requirements. As mentioned previously, there is no requirement that the fluorescent dye(s) selected for the method described herein absorb light at any particular wavelength or range of wavelengths or emit fluorescence at any particular wavelength or range of wavelengths. The following table sets forth representative wavelengths for sources of light and fluorescent dyes that can be used at these wavelengths.

TABLE 1

| Wavelength of source of light (nm) | Category of fluorescent dye | Commercially available examples of the fluorescent dye |
|---|---|---|
| 405 | Blue fluorescent nucleic acid stain | SYTO ® 40 |
| | | SYTO ® 41 |
| | | SYTO ® 42 |
| | | SYTO ® 43 |
| | | SYTO ® 44 |
| | | SYTO ® 45 |
| | | Auramine O |
| 488 | Green fluorescent nucleic acid stain | SYTO ® 9 |
| | | SYTO ® 10 |
| | | SYTO ® 13 |
| | | SYTO ® 16 |
| | | SYTO ® 21 |
| | | SYTO ® 23 |
| | | SYTO ® 24 |
| | | SYTO ® 26 |
| | | SYTO ® 27 |
| | | SYTO ® BC |
| | | Acridine orange |
| | | SYBR ® 11 |
| 532 | Orange fluorescent nucleic acid stain | SYTO ® 80 |
| | | SYTO ® 81 |
| | | SYTO ® 82 |
| | | SYTO ® 83 |
| | | SYTO ® 86 |
| | | Dihydroethidium |
| | | Hexidium iodide |

TABLE 1-continued

| Wavelength of source of light (nm) | Category of fluorescent dye | Commercially available examples of the fluorescent dye |
|---|---|---|
| 594 | Red fluorescent nucleic acid stain | SYTO® 64 |
| 633 | Red fluorescent nucleic acid stain | SYTO® 17<br>SYTO® 59<br>SYTO® 60<br>SYTO® 61<br>SYTO® 62<br>SYTO® 63 |

Dyes having the trademark SYTO® are commercially available from Molecular Probes, Inc., Eugene, Oreg. Dyes having the trademark SYBR® are commercially available from Molecular Probes, Inc., Eugene, Oreg.

The following table sets forth criteria that are suitable for selecting a source of light and ranges of wavelengths for fluorescent dyes that are suitable for use in the method described herein.

TABLE 2

| Range of wavelengths (approximate) for source of light (nm) | Absorption maxima (approximate) of fluorescent dye based on wavelength of source of light (nm) | Fluorescent emission maxima (approximate) of fluorescent dye based on wavelength of source of light (nm) |
|---|---|---|
| 400-455 | 420-460 | 440-490 in the presence of DNA |
| 480-530 | 480-530 | 490-560 in the presence of DNA, RNA, or DNA plus RNA |
| 530-570 | 530-570 | 540-590 in the presence of DNA |
| 590-660 | 590-660 | 615-680 in the presence of DNA |

Precise absorption maxima and fluorescent emission maxima can be found in the following publications, all of which are incorporated herein by reference:

SYTO® Blue Fluorescent Nucleic Acid Stains, Molecular Probes Product Information, Revised: 15 Jan. 2001
SYTO® Green-Fluorescent Nucleic Acid Stains, Invitrogen™, Molecular Probes®, Revised: 28 Apr. 2008
SYTO® Orange Fluorescent Nucleic Acid Stains, Molecular Probes Product Information, Revised: 13 Jan. 2001
SYTO® Red Fluorescent Nucleic Acid Stains, Molecular Probes Product Information, Revised: 15 Jan. 2001

Several photodiodes or photomultiplier tubes or both photodiodes and photomultiplier tubes can be used to detect light scattering of each cell passing through the flow cell. Two or more photodiodes or photomultiplier tubes can be installed for measuring axial light loss (ALL), which measures the total light lost from the laser beam at from about 0° to about 1° when a particle passes through the beam, and intermediate angle scatter (IAS), which measures low angle light scatter (3°-15°). Two or more photomultiplier tubes can be installed for detecting polarized light scatter (PSS) and depolarized light scatter (DSS).

Additional photomultiplier tubes can be used to measure fluorescence at appropriate wavelengths or ranges of wavelengths, depending on the choice of fluorescent dye(s) and the choice of wavelength of the source of light. Each event captured by the system described herein would thus possess a plurality of dimensions of information, such as ALL, one or more IAS signals, PSS, DSS, and one or more fluorescent signals. For example, one IAS detection channel can be used for smaller angles (i.e., 3° to 6°) and another IAS detection channel can be used for larger angles (i.e., 6° to 10°). For fluorescence detection, one detection channel can be used for complexes of a fluorescent dye and DNA and one detection channel can be used for complexes of a fluorescent dye and RNA, because complexes of fluorescent dye and DNA emit a fluorescent signal at a wavelength that is different from the wavelength of the fluorescent signal emitted by complexes of fluorescent dye and RNA. The information from these detection channels can be used for further analysis of the cells in a sample of blood.

The following non-limiting examples further illustrate the method described herein.

EXAMPLE 1

This example illustrates the capture of white blood cells and bright platelet events by means of a fluorescent trigger, following interactions of the sample of blood with dye molecules.

The following procedure, including apparatus, parameters, reagents, including diluents, was used for EXAMPLES 1-5, inclusive.

A fluorescent dye was used to stain and differentiate white blood cells (by means of DNA staining), nucleated red blood cells (by means of DNA staining), and reticulocytes (by means of RNA staining). A fluorescent trigger was used to generate two data blocks, thereby separating the highly fluorescent cells (white blood cells and nucleated red blood cells) from low fluorescent events (red blood cells and platelets). The first data block was used to analyze red blood cells, platelets, and reticulocytes. The second data block was used to identify white blood cells and nucleated red blood cells.

Each cell population was identified by means of a 407 nm flow cytometry optical bench and four channels of scattered light: 0° (ALL), 7° (IAS), 90° (PSS), and 90° depolarized (DSS). The fluorescence detector was a photomultiplier tube capable of detecting 450 nm to 580 nm. The source of light is a 407 nm solid-state laser (50 mW maximum, 40 mW actually used). The size of the flow cell was 290 μm (length)×210 μm (width). The laser scanned the length (290 μm) of the flow cell. A laser rastering system was used to enable high throughput (greater than 300,000 cells per second) under lysis-free conditions. See U.S. patent application Ser. No. 12/767,611, filed Apr. 26, 2010, and entitled METHOD FOR DISCRIMINATING RED BLOOD CELLS FROM WHITE BLOOD CELLS BY USING FORWARD SCATTERING FROM A LASER IN AN AUTOMATED HEMATOLOGY ANALYZER, previously incorporated herein by reference, for details of the laser rastering system. However, a laser rastering system is not required to carry out the method described herein. Similarly, a 407 nm flow cytometry optical bench is not required to carry out the method described herein. Other wavelengths, other lasers, and other sources of light can be used to carry out the method described herein.

A fresh sample of blood was diluted to a concentration of 1 part blood per 50 parts diluent to serve as the reference and calibration standard. The diluted sample of blood, at a red blood cell concentration of approximately 0.1 million red blood cells/μL, should exhibit little or no coincidences on the flow cytometer of the hematology analyzer. Three to six runs were conducted with the CELL-DYN® Sapphire™ hematology analyzer and three to six runs were conducted under the lysis-free conditions described herein. For EXAMPLES 1-5, inclusive:

(1) Flow rate (red blood cells)=Flow rate (total blood cells) times percentage of red blood cells, where percentage of red blood cells equals the fraction of events attributed to red blood cells.
(2) Calibration factor=Flow rate (red blood cells) divided by concentration of red blood cells
(3) Cell count=Flow rate (sample) divided by the calibration factor
(4) The diluent was CELL-DYN® Sapphire™ diluent/sheath
(5) The fluorescent dye was SYTO® 41, 17 micromolar, commercially available from Molecular probes, Inc., Eugene Oreg.
(6) The ratio of the sample of blood to the dye reagent to the diluent/sheath was approximately 1 part by volume sample of blood to 7.5 parts by volume dye reagent to 77.5 parts by volume diluent/sheath.
(7) Duration of incubation was 30 seconds at a temperature of about 41° C. (±1° C.) to allow sufficient staining of cells having nucleic acid content, i.e., white blood cells, nucleated red blood cells, and reticulocytes.
(8) Conditions for acquisition of data:
  (A) Red blood cell file (0.2 second, IAS trigger=75, for analysis of red blood cells, reticulocytes, and platelets)
  (B) White blood cell file (20 seconds, FL trigger=75, for analysis of white blood cells, white blood cell differential, and nucleated red blood cells)

The measurement process was initiated immediately following incubation of the sample. The cell stream, surrounded by the sheath solution, was introduced to the flow cell. The flow velocity of the sheath was 6 m/sec, which resulted in approximately 300,000 red blood cell events passing through the flow cell per second (for a blood sample having $5 \times 10^6$ red blood cells/µL). A laser rastering system, described in U.S. patent application Ser. No. 12/767,611, filed Apr. 26, 2010, and entitled METHOD FOR DISCRIMINATING RED BLOOD CELLS FROM WHITE BLOOD CELLS BY USING FORWARD SCATTERING FROM A LASER IN AN AUTOMATED HEMATOLOGY ANALYZER, previously incorporated herein by reference, was used to scan the stream of cells. The spot size of the laser beam was 20 µm×10 µm. The size of the sample core stream is typically 65 µm (width)×19 µm (depth).

The data, including the light scattering signals (ALL, IAS, PSS and DSS) and fluorescence signals (FL), were collected for each captured event. A data block, triggered by IAS, was collected in 0.2 second for all cellular particles. Electronic noises were minimized by the IAS trigger. 57,649 red blood cell events, equivalent to a red blood cell count of $4.4 \times 10^6$ red blood cells/µL without coincidence correction, and 2,082 PLT events, equivalent to a platelet count of $157 \times 10^3$ platelets/µL without coincidence correction, were captured for a whole blood specimen having $4.8 \times 10^6$ red blood cells/µL and $218 \times 10^3$ platelets/µL PLT (reference values were measured by a CELL-DYN® Sapphire™ hematology analyzer). The discrepancies were a result of the approximately 10% coincidences involving red blood cells only and the approximately 20-30% coincidences involving red blood cells and platelets observed for all of the samples of blood. Reticulocytes (2.5%) were also quantified by using fluorescence in the same runs (% Reticulocytes=3.1% as referenced by the CELL-DYN® Sapphire™ hematology analyzer).

Figure 3:
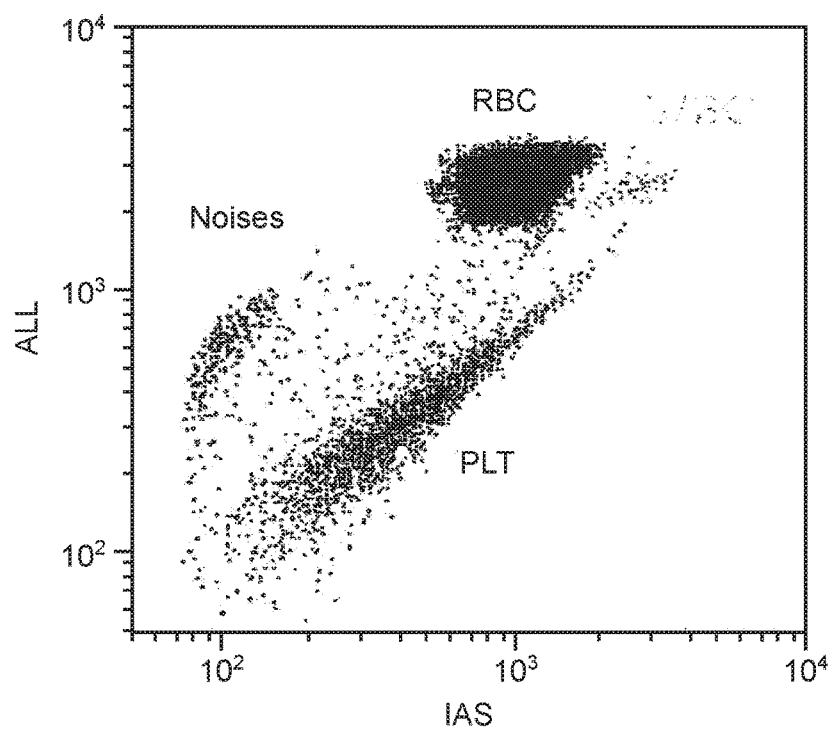
FIG. 3 is a cytogram illustrating the separation of major cell populations of a sample of whole blood, i.e., red blood cells (RBC), platelets (PLT), and white blood cells (WBC) by means of axial light loss (ALL) and intermediate angle scatter (IAS) of light. Noise is also depicted.

The cytogram of FIG. 3 illustrates the separation of populations of major cells of a sample of whole blood, i.e., red blood cells, platelets, and white blood cells, by means of axial light loss (ALL) and intermediate angle scatter (IAS) of light.

Figure 4:
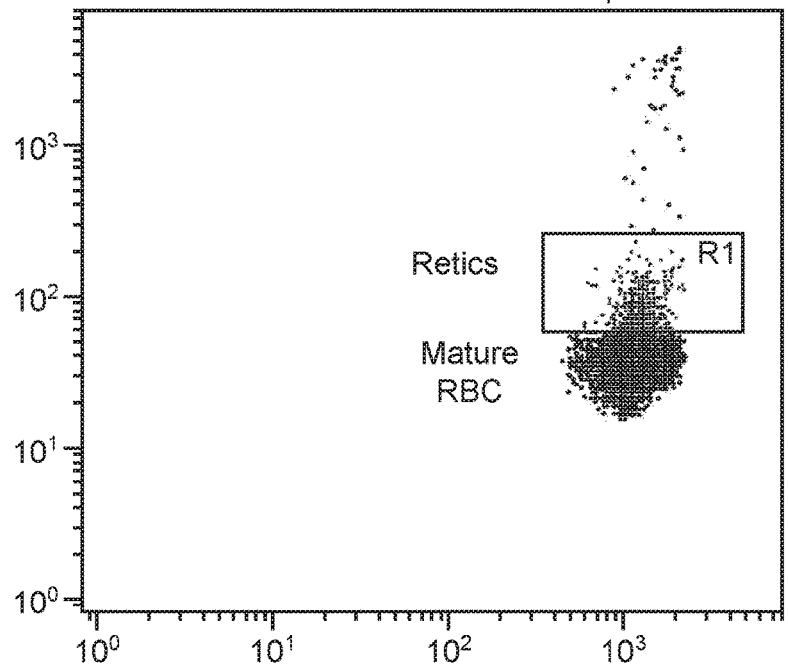
FIG. 4 is a cytogram illustrating the further separation of reticulocytes (Retics) from mature red blood cells (RBC) by means of fluorescence, following interaction of a fluorescent dye and RNA.

The cytogram of FIG. 4 illustrates the further separation of reticulocytes from mature red blood cells by means of fluorescence, following interaction of a fluorescent dye and RNA.

EXAMPLE 2

This example illustrates that the method described herein separates red blood cells and platelets from other components of a sample of blood. The sample set included 103 specimens of whole blood, namely, 35 normal samples, 68 abnormal samples, with 12 samples containing or suspected of containing nucleated red blood cells. Two runs were carried out for each sample of blood; CELL-DYN® Sapphire™ hematology analyzer was used as the primary reference, i.e., to determine to what degree the method described herein compares with a hematology analyzer that requires a lysing agent.

The apparatus, diluent, fluorescent dye, preparation of the sample, and conditions for measurement were the same as that described in EXAMPLE 1.

Figure 5:
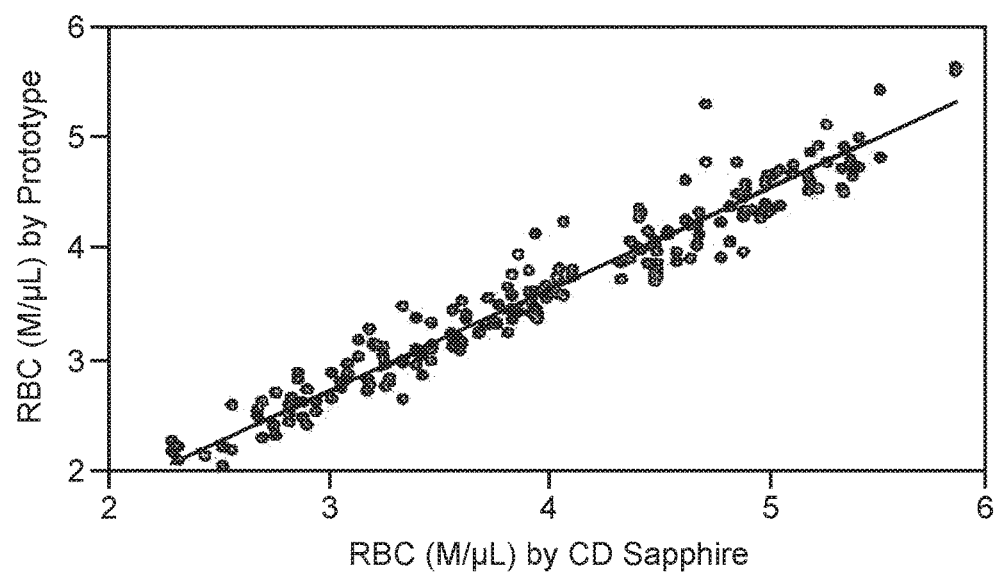
FIG. 5 is a plot illustrating the correlation between the CELL-DYN® Sapphire™ hematology analyzer and a hematology analyzer using the method described herein for red blood cells (RBC). The symbol M in the concentration scale represents $1 \times 10^6$.

The plot in FIG. 5 illustrates the correlation between the CELL-DYN® Sapphire™ hematology analyzer and a hematology analyzer using the method described herein for counting red blood cells. The slope of the best linear fit was 0.899 ($R^2$=0.933). The approximately 10% bias was due to coincidences between red blood cells in the runs.

Figure 6:
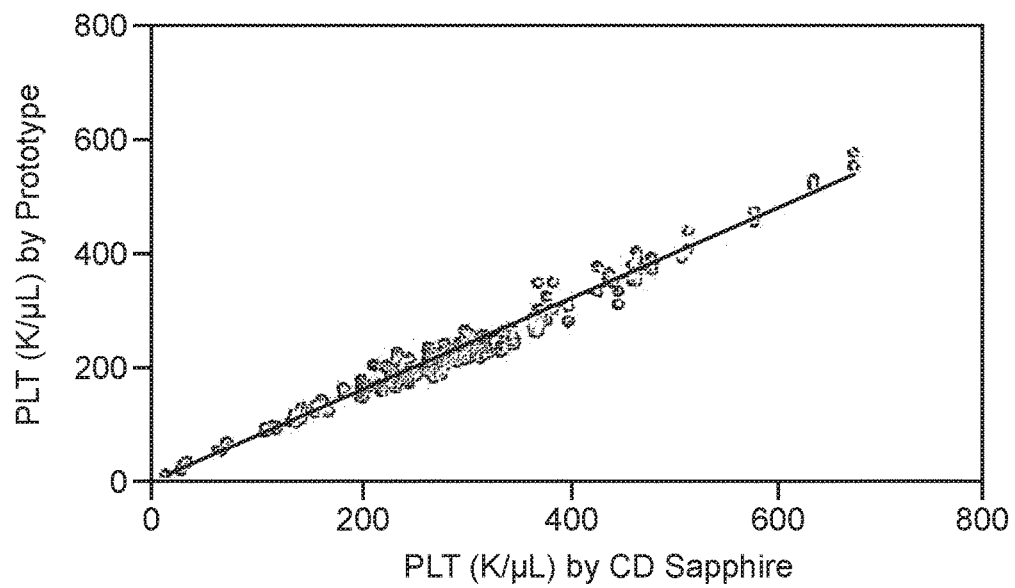
FIG. 6 is a plot illustrating the correlation between the CELL-DYN® Sapphire™ hematology analyzer and a hematology analyzer using the method described herein for platelets (PLT). The symbol K in the concentration scale represents $1 \times 10^3$.

The plot in FIG. 6 illustrates the correlation between the CELL-DYN® Sapphire™ hematology analyzer and a hematology analyzer using the method described herein for counting platelets. The slope of the best linear fit was 0.783 ($R^2$=0.971). The approximately 20% to 30% bias was due to coincidences between red blood cells and platelets in the runs.

EXAMPLE 3

This example illustrates the analysis of a white blood cell differential. The apparatus, diluent, fluorescent dye, preparation of the sample, and conditions for measurement were the same as that described in EXAMPLE 1.

The data, triggered by fluorescent signals (FL), were collected in 20 seconds for all events having a fluorescent signal (FL) higher than 75, including all white blood cells, nucleated red blood cells, if there were any, and a small fraction of bright platelets. 8586 white blood cell events, equivalent to a white blood cell count of $6.48 \times 10^3$ white blood cells/µL, were captured for a specimen of whole blood having a white blood cell count of $6.29 \times 10^3$ white blood cells/µL (based on the reference value from a CELL-DYN® Sapphire™ hematology analyzer). The subpopulations of white blood cells, including neutrophils, lymphocytes, monocytes, and eosinophils, were analyzed by means of the signals obtained from a plurality of optical channels.

Figure 7:
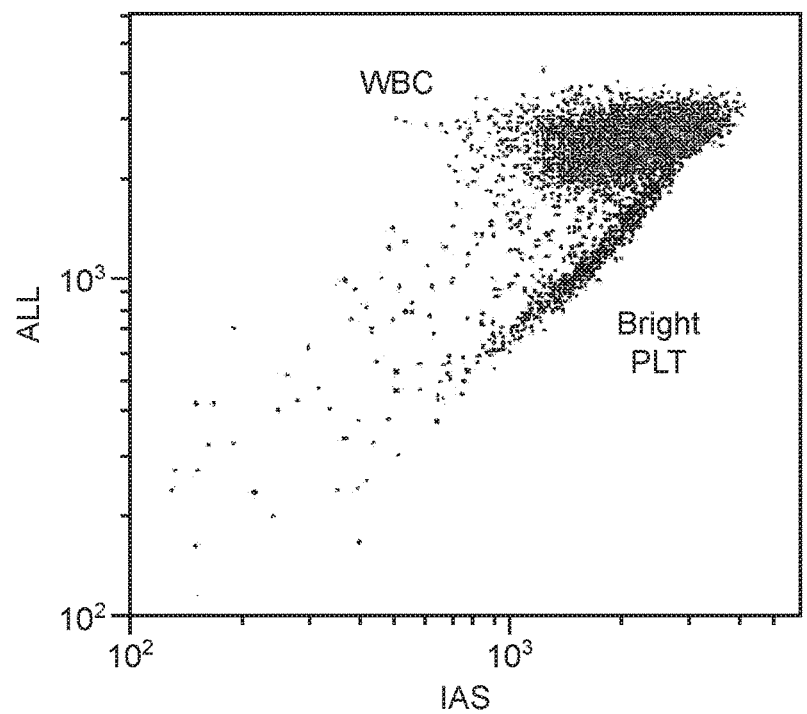
FIG. 7 is a cytogram illustrating separation of fluorescent (bright) platelets (PLT) from white blood cells (WBC) of a sample of whole blood by means of axial light loss (ALL) and intermediate angle scatter (IAS) of light.

The cytogram of FIG. 7 illustrates separation of white blood cells from fluorescent (bright) platelets of a sample of whole blood by means of axial light loss (ALL) and intermediate angle scatter (IAS) of light.

Figure 8:
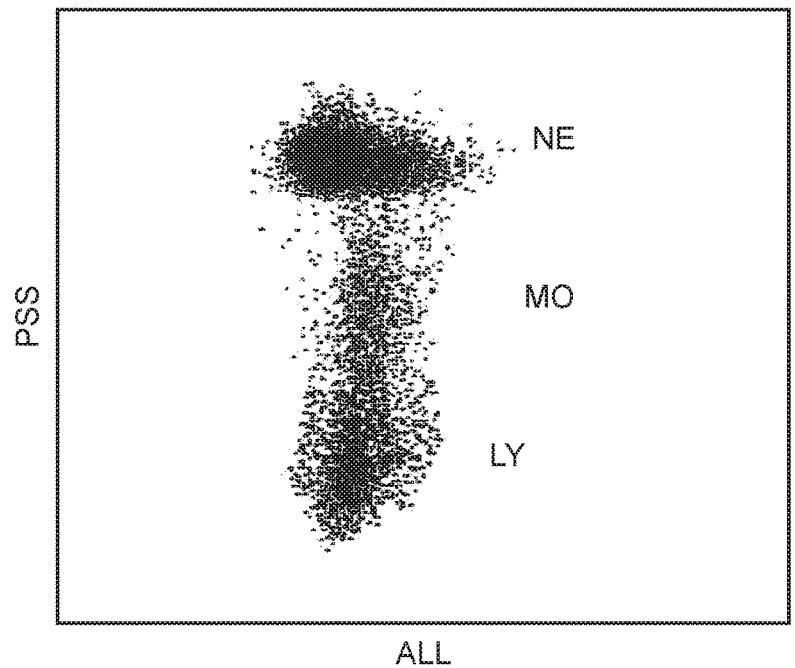
FIG. 8 is a cytogram illustrating the three major subpopulations of white blood cells, namely, neutrophils (NE), lymphocytes (LY), and monocytes (MO) by means of polarized side scatter (PSS) and axial light loss (ALL).

The cytogram of FIG. 8 illustrates the three major subpopulations of white blood cells, namely, neutrophils (NE), lymphocytes (LY), and monocytes (MO) by means of polarized side scatter (PSS) and axial light loss (ALL) of light.

Figure 9:
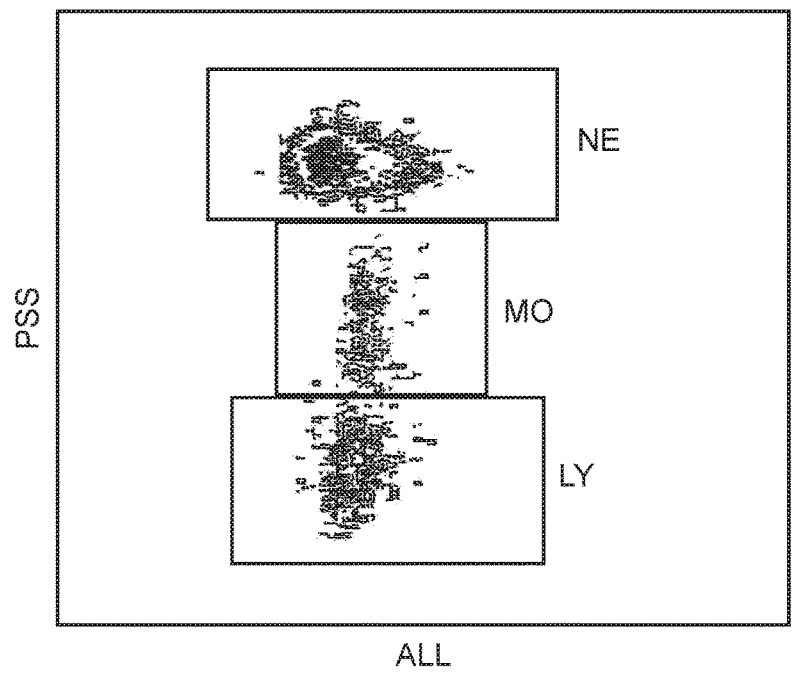
FIG. 9 is a cytogram illustrating the three major subpopulations of white blood cells, namely, neutrophils (NE), lymphocytes (LY), and monocytes (MO) by means of polarized side scatter (PSS) and axial light loss (ALL).

The cytogram of FIG. 9 illustrates the three major subpopulations of white blood cells, namely, neutrophils (NE), lymphocytes (LY), and monocytes (MO) by means of polarized side scatter (PSS) and axial light loss (ALL) of light.

Figure 10:
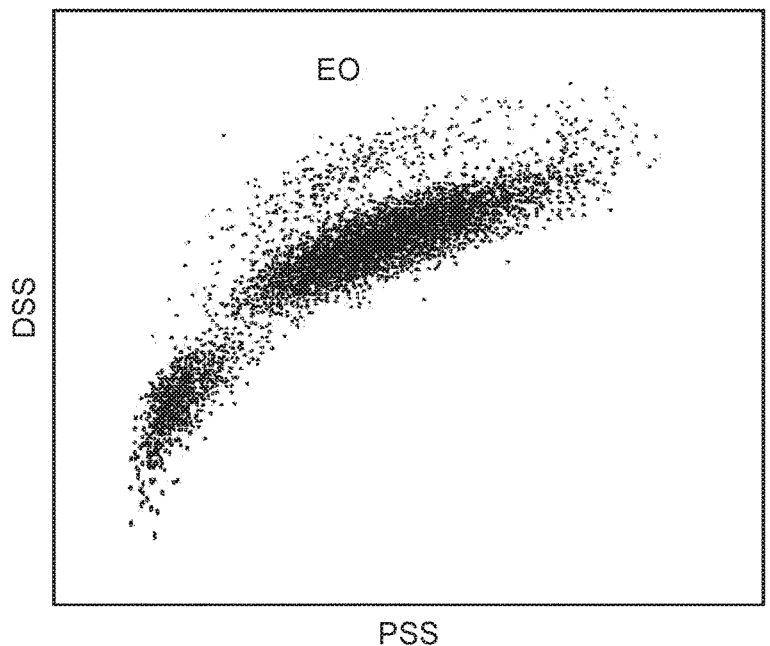
FIG. 10 is a cytogram illustrating the separation of eosinophils (EO) from the remaining white blood cells by means of depolarized (DSS) and polarized side scatter (PSS).

The cytogram of FIG. 10 illustrates the separation of eosinophils (EO) from the remaining white blood cells by means of depolarized side scatter (DSS) and polarized side scatter (PSS) of light.

The values of white blood cell differential are listed in the following table.

TABLE 3

| White blood cell subpopulation* | Amount of component as determined by CELL-DYN ® Sapphire ™ hematology analyzer (%) | Amount of component as determined by method of Example 3 (lysis-free assay) (%) |
| --- | --- | --- |
| Neutrophils (NE) | 61 | 59 |
| Lymphocytes (LY) | 21 | 24 |
| Monocytes (MO) | 15 | 13 |
| Eosinophils (EO) | 3 | 4 |

*Basophils were not reported on account of limitations of the optical channels.

EXAMPLE 4

This example illustrates how well the method described herein correlates with a CELL-DYN® Sapphire™ hematology analyzer for the analysis of a white blood cell differential. The apparatus, diluent, fluorescent dye, preparation of the sample, and conditions for measurement were the same as that described in EXAMPLE 1.

The data, triggered by fluorescent signals (FL), were collected in 20 seconds for all events having a fluorescent signal (FL) higher than 75, including all white blood cells, nucleated red blood cells, if there were any, and a small fraction of bright platelets. 8586 white blood cell events, equivalent to a white blood cell count of $6.48 \times 10^3$ white blood cells/µL, were captured for a specimen of whole blood having a white blood cell count of $6.29 \times 10^3$ white blood cells/µL (based on the reference value from a CELL-DYN® Sapphire™ hematology analyzer). The subpopulations of white blood cells, including neutrophils, lymphocytes, monocytes, and eosinophils, were analyzed by means of the signals obtained from a plurality of optical channels.

Figure 11:
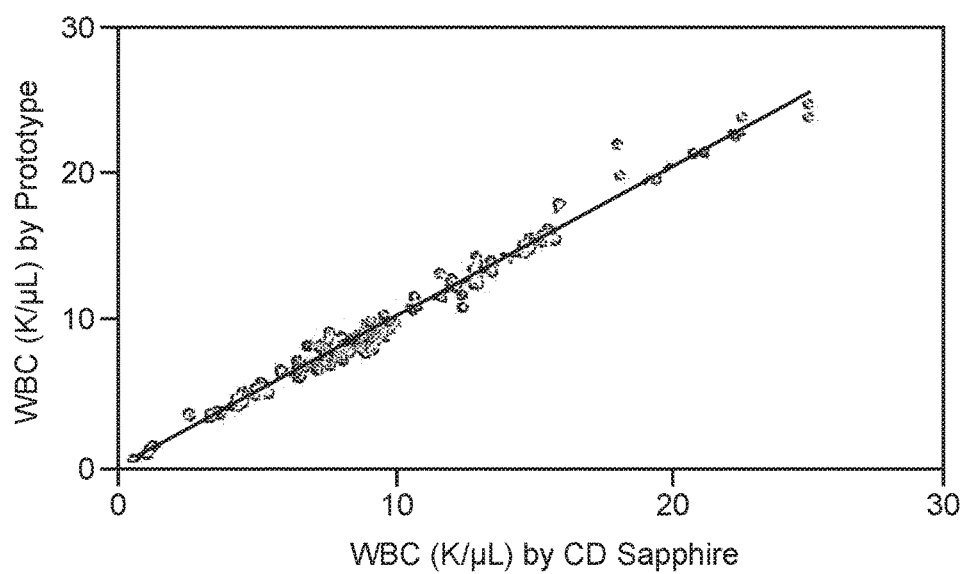
FIG. 11 is a plot illustrating the correlation between the CELL-DYN® Sapphire™ hematology analyzer and a hematology analyzer using the method described herein for white blood cells (WBC). The symbol K in the concentration scale represents $1 \times 10^3$.

The plot in FIG. 11 illustrates the correlation between the CELL-DYN® Sapphire™ hematology analyzer and a hematology analyzer using the method described herein for white blood cells. The slope of the best linear fit was 1.019 ($R^2$=0.988).

Figure 12:
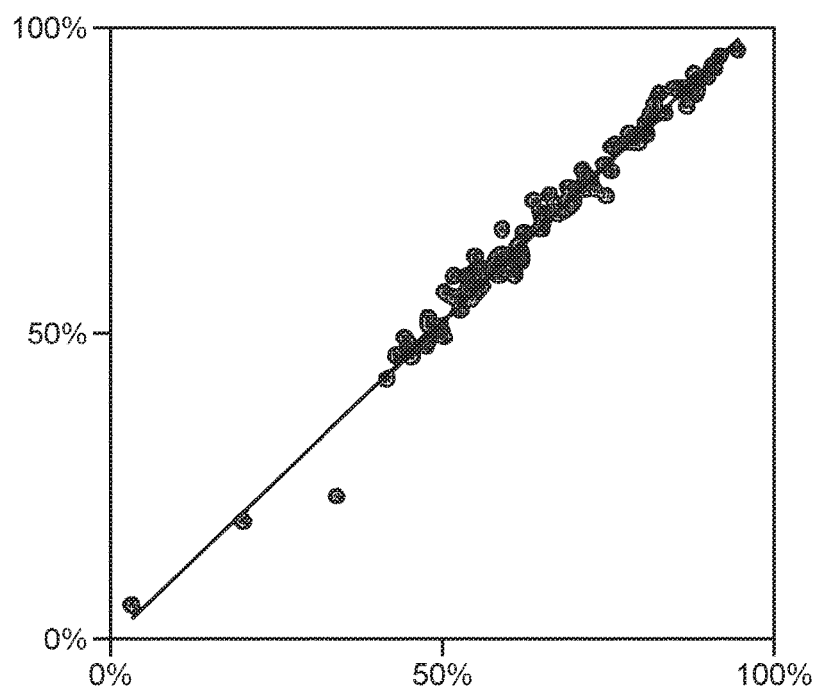
FIG. 12 is a plot illustrating the correlation between the CELL-DYN® Sapphire™ hematology analyzer and a hematology analyzer using the method described herein for neutrophils.

The plot in FIG. 12 illustrates the correlation between the CELL-DYN® Sapphire™ hematology analyzer and a hematology analyzer using the method described herein for neutrophils. The slope of the best linear fit was 1.024 ($R^2$=0.979).

Figure 13:
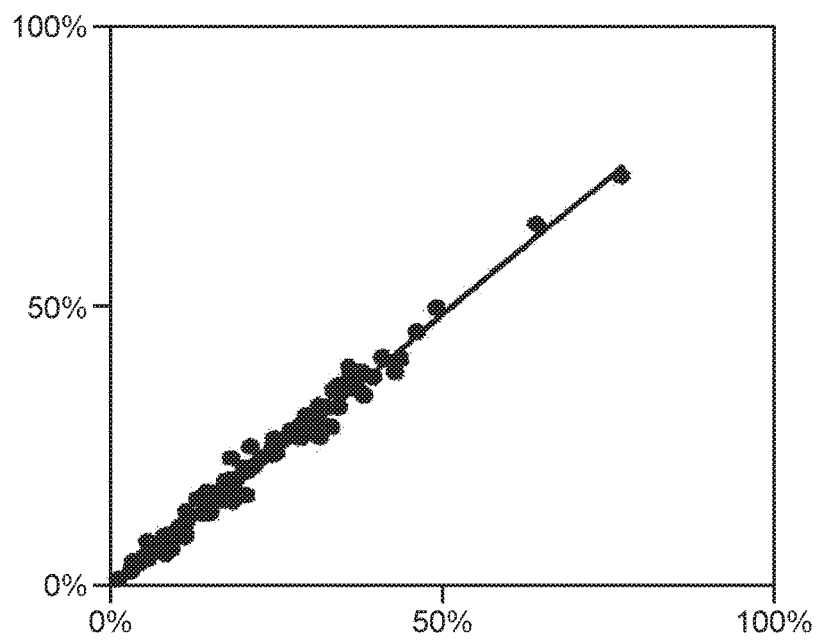
FIG. 13 is a plot illustrating the correlation between the CELL-DYN® Sapphire™ hematology analyzer and a hematology analyzer using the method described herein for lymphocytes.

The plot in FIG. 13 illustrates the correlation between the CELL-DYN® Sapphire™ hematology analyzer and a hematology analyzer using the method described herein for lymphocytes. The slope of the best linear fit was 0.967 ($R^2$=0.983).

Figure 14:
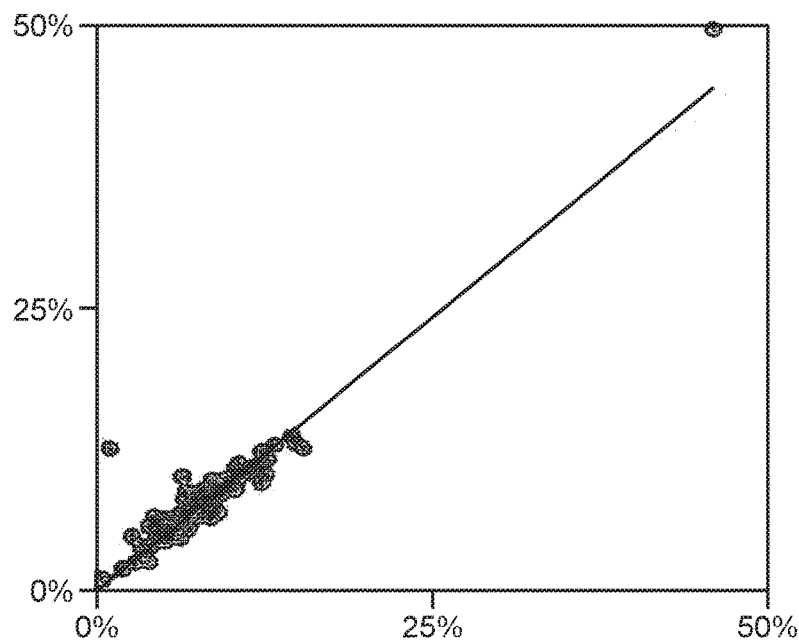
FIG. 14 is a plot illustrating the correlation between the CELL-DYN® Sapphire™ hematology analyzer and a hematology analyzer using the method described herein for monocytes.

The plot in FIG. 14 illustrates the correlation between the CELL-DYN® Sapphire™ hematology analyzer and a hematology analyzer using the method described herein for monocytes. The slope of the best linear fit was 0.959 ($R^2$=0.890).

Figure 15:
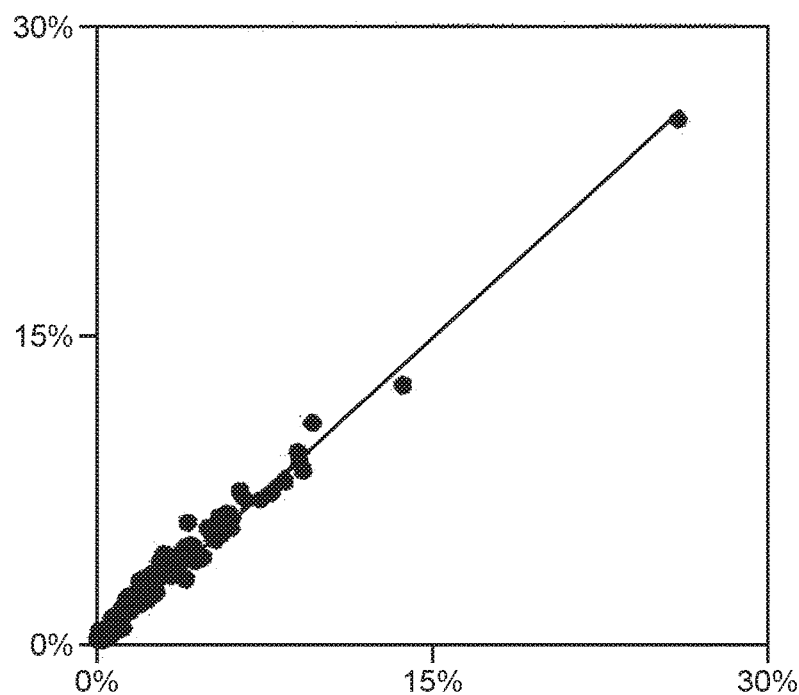
FIG. 15 is a plot illustrating the correlation between the CELL-DYN® Sapphire™ hematology analyzer and a hematology analyzer using the method described herein for eosinophils.

The plot in FIG. 15 illustrates the correlation between the CELL-DYN® Sapphire™ hematology analyzer and a hematology analyzer using the method described herein for eosinophils. The slope of the best linear fit was 0.994 ($R^2$=0.982).

EXAMPLE 5

This example illustrates the counting of nucleated red blood cells by the method described herein. The apparatus, diluent, fluorescent dye, preparation of the sample, and conditions for measurement were the same as that described in EXAMPLE 1.

The data, triggered by fluorescence signals (FL), were collected in 20 seconds for all events having a fluorescent signal (FL) higher than 75, including all white blood cells, nucleated red blood cells, if there were any, and a small fraction of bright platelets. 8586 white blood cell events, equivalent to a white blood cell count of $6.48 \times 10^3$ white blood cells/µL, were captured for a specimen of whole blood having a white blood cell count of $6.29 \times 10^3$ white blood cells/µL (based on the reference value from a CELL-DYN® Sapphire™ hematology analyzer). The subpopulations of white blood cells, including neutrophils, lymphocytes, monocytes, and eosinophils, were analyzed by means of the signals obtained from a plurality of optical channels.

A sample of whole blood having a confirmed content of nucleated red blood cells (nucleated red blood cells/white blood cells=3.99% as measured by a CELL-DYN® Sapphire™ hematology apparatus) was analyzed to determine the concentration of nucleated red blood cells according to the method described herein.

Figure 16:
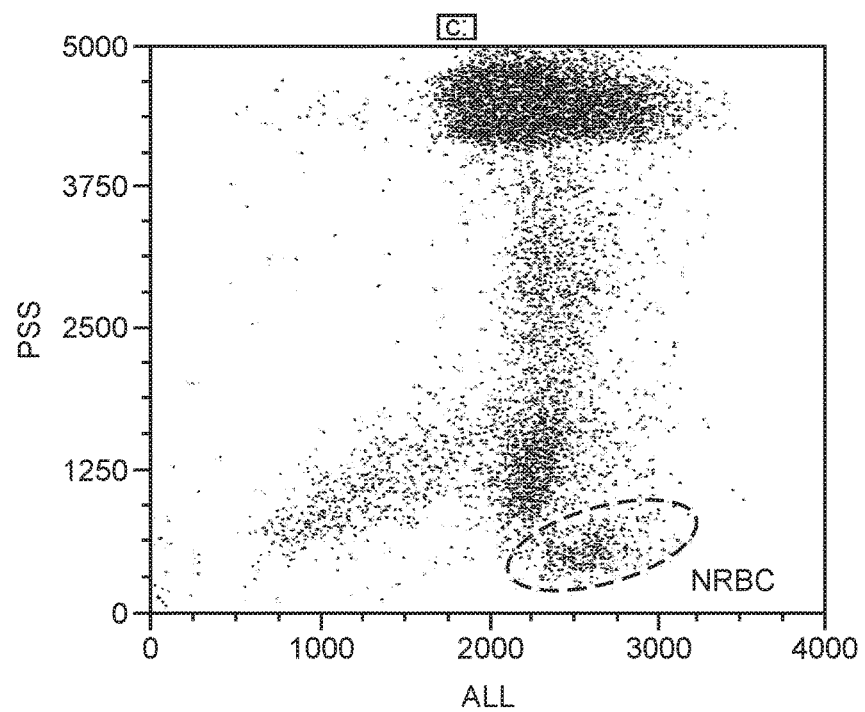
FIG. 16 is a cytogram illustrating a method of distinguishing nucleated red blood cells (NRBC) from white blood cells.

The cytogram in FIG. 16 illustrates nucleated red blood cell events as a separate population from the white blood cells. The cytogram is a plot of polarized side scatter (PSS) against axial light loss (ALL) of light. The ratio of nucleated red blood cells to white blood cells was calculated to be 4.5%.

EXAMPLE 6

This example illustrates the use of a source of light different from that used in EXAMPLES 1-5, inclusive, and a fluorescent dye different from that used in EXAMPLES 1-5, inclusive, for an analysis of a white blood cell differential. The following procedure, including apparatus, parameters, reagents, including diluents, was used for Example 6.

This example illustrates capturing of white blood cells and bright platelet events by means of a fluorescent trigger, following interactions of the sample with dye molecules.

A fluorescent dye, SYBR® 11, commercially available from Molecular probes, Inc., Eugene Oreg., was used to stain and differentiate white blood cells (DNA), nucleated red blood cells (DNA), and reticulocytes (RNA). The data block thus collected was used to identify white blood cells and nucleated red blood cells.

Each cell population was identified by means of a 488 nm flow cytometry optical bench and four channels of scattered light: 0° (ALL), 7° (IAS), and 90° (PSS). The 488 nm source of light was a solid-state diode laser (20 mW). The size of the flow cell was 400 µm (length)×160 µm (width). The laser scanned the length (400 µm) of the flow cell. The detection devices included a plurality of optical channels, including ALL, IAS, and PSS, and a photomultiplier tube detector for fluorescence (FL1, 515 nm to 545 nm).

Preparation of the sample involved a single dilution of the sample of blood with the fluorescent dye and the diluent/sheath. The dilution ratio was approximately 1 part by volume sample of blood to 3.2 parts by volume fluorescent dye reagent to 31 parts by volume diluent/sheath. The diluted sample of blood was incubated at a temperature of 40° C. (±1° C.) for 32 seconds to allow sufficient staining of cells having a content of nucleic acids, i.e., white blood cells, nucleic red blood cells, and reticulocytes.

The measurement process was initiated immediately following incubation of the sample. The cell stream, surrounded by the sheath solution, was introduced to the flow cell. The flow velocity of the sheath flow was 6 m/s, which resulted in approximately 200 white blood cell events passing through the flow cell per second (for a sample of blood having $5 \times 10^3$ white blood cells/μL). The spot size of the laser beam was 65 μm×17 μm. The size of the sample core stream is typically 70 μm (width)×5 μm (depth). The total measurement time was approximately nine (9) seconds.

Figure 17:
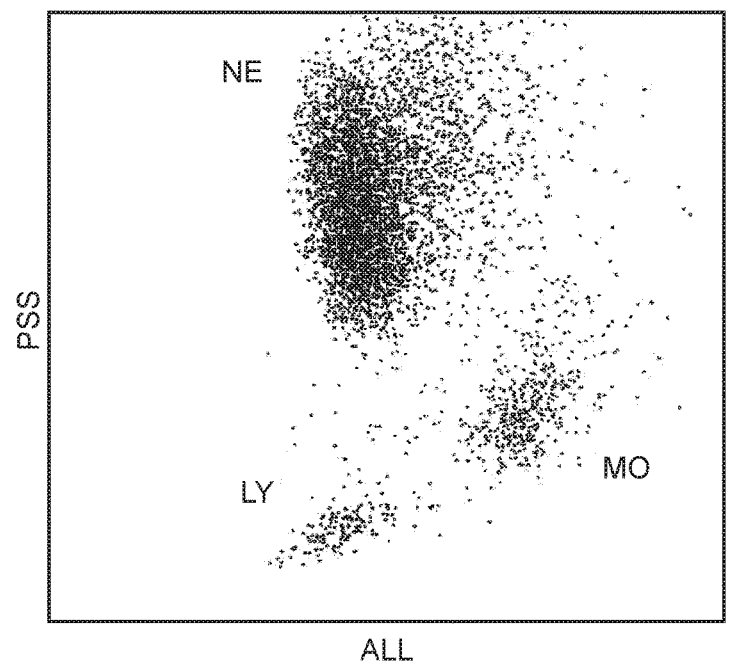
FIG. 17 is a cytogram illustrating a white blood cell differential analysis wherein neutrophils (NE), monocytes (MO), and lymphocytes (LY) are separated from the other white blood cell components.

The data, including the light scattering signals (ALL, IAS, and PSS) and fluorescence signals (FL1), were collected for each event triggered by fluorescence. 5760 white blood cell events were captured for a whole blood specimen having $16 \times 10^3$ white blood cells. The subpopulations of white blood cells, including neutrophils, lymphocytes, and monocytes, were differentiated by means of cytograms. The cytogram of FIG. 17 illustrates white blood cell differentiation of a sample of whole blood by means of the method described herein.

The values of white blood cell differential are listed in the following table.

TABLE 4

| White blood cell subpopulation* | Amount of component as determined by CELL-DYN ® Sapphire ™ hematology analyzer (%) | Amount of component as determined by method of Example 6 (%) |
|---|---|---|
| Neutrophils | 86 | 88 |
| Lymphocytes | 4 | 3 |
| Monocytes | 9 | 9 |

*Eosinophils and basophils were not reported on account of limitations of the optical channels.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. An automated hematology analyzer for counting cells in a sample of whole blood, said analyzer comprising:
   an excitation source positioned to excite particles within the blood sample; and
   a plurality of detectors including an axial light loss detector positioned to measure axial light loss from the excited blood sample, an intermediate angle scatter detector positioned to measure intermediate angle scatter from the excited blood sample, a side scatter detector positioned to measure 90° side scatter from the excited blood sample, and a fluorescence detector positioned to measure fluorescence emitted from the excited blood sample;
   a processor; and
   a non-transitory computer-readable memory medium comprising instructions that when executed cause the processor to:
   dilute a sample of whole blood with a diluent, wherein the sample comprises a plurality of white blood cells, nucleated red blood cells, red blood cells, platelets, and reticulocytes;
   contact the sample with at least one fluorescent dye that specifically binds to and stains one or more nucleic acids in the white blood cells, the nucleated red blood cells, and/or the reticulocytes in the sample;
   generate a plurality of events, wherein each event comprises a plurality of light scattering signals and a fluorescence emission signal generated by a cell in the sample;
   separate the events into two data blocks using a fluorescent trigger, wherein the first data block includes events having a fluorescence emission signal that is below the fluorescent trigger, and the second data block includes events having a fluorescence emission signal that is above the fluorescent trigger;
   analyze the events in the first data block to count the number of red blood cells, platelets, and reticulocytes in the sample; and
   analyze the events in the second data block to count the number of white blood cells and nucleated red blood cells in the sample.

2. The automated hematology analyzer of claim 1, wherein the at least one fluorescent dye specifically binds to and stains a nucleic acid in the reticulocytes.

3. The automated hematology analyzer of claim 1, wherein the excitation source is a laser.

4. The automated hematology analyzer of claim 1, wherein the source of light has a wavelength of from 350 nm to 700 nm.

5. The automated hematology analyzer of claim 4, wherein the source of light has a wavelength of from 400 nm to 455 nm.

6. The automated hematology analyzer of claim 4, wherein the source of light has a wavelength of from 480 nm to 530 nm.

7. The automated hematology analyzer of claim 4, wherein the source of light has a wavelength of from 530 nm to 570 nm.

8. The automated hematology analyzer of claim 4, wherein the source of light has a wavelength of from 590 nm to 660 nm.

9. The automated hematology analyzer of claim 1, wherein the at least one fluorescent dye has an absorption maximum of from 420 nm to 460 nm.

10. The automated hematology analyzer of claim 1, wherein the at least one fluorescent dye has an absorption maximum of from 480 nm to 530 nm.

11. The automated hematology analyzer of claim 1, wherein the at least one fluorescent dye has an absorption maximum of from 530 nm to 570.

12. The automated hematology analyzer of claim 1, wherein the at least one fluorescent dye has an absorption maximum of from 590 to 660 nm.

13. The automated hematology analyzer of claim 1, wherein the at least one fluorescent dye has an emission maximum of from 440 nm to 490 nm in the presence of DNA.

14. The automated hematology analyzer of claim 1, wherein the at least one fluorescent dye has an emission maximum of from 490 nm to 560 nm in the presence of DNA or RNA or both DNA and RNA.

15. The automated hematology analyzer of claim 1, wherein the at least one fluorescent dye has an emission maximum of from 540 nm to 590 nm in the presence of DNA.

16. The automated hematology analyzer of claim 1, wherein the at least one fluorescent dye has an emission maximum of from 615 nm to 680 nm in the presence of DNA.

17. The automated hematology analyzer of claim 1, wherein the hematology analyzer is configured to analyze the events in the second data block to count the number of cells in each of a plurality of white blood cell subpopulations.

18. The automated hematology analyzer of claim 1, wherein the analyzer employs no more than two reagents, said reagents being a diluent and a fluorescent dye.

19. The automated hematology analyzer of claim 10, wherein contacting the sample with at least one fluorescent dye comprises diluting the sample of whole blood in a diluent in which the fluorescent dye is pre-diluted.

20. The automated hematology analyzer of claim 10, wherein contacting the sample with at least one fluorescent dye occurs after diluting the sample of whole blood with the diluent.

21. The automated hematology analyzer of claim 1, wherein the hematology analyzer is configured to contact the sample with a fluorescent dye and/or stain that fluorescently labels platelets in the sample, and analyze events from the second data block to count the number of platelets in the sample.

* * * * *